(12) United States Patent
Steiger

(10) Patent No.: US 7,060,071 B2
(45) Date of Patent: Jun. 13, 2006

(54) COUPLING DEVICE FOR INSTRUMENT COMPONENTS

(76) Inventor: Peter Steiger, Wysshölzlistrasse 34, Herzogenbuchsee (CH) CH-3360

( * ) Notice: Subject to any disclaimer, the term of this patent is extended or adjusted under 35 U.S.C. 154(b) by 698 days.

(21) Appl. No.: 10/235,728

(22) Filed: Sep. 6, 2002

(65) Prior Publication Data
US 2003/0055432 A1    Mar. 20, 2003

Related U.S. Application Data

(63) Continuation of application No. PCT/CH00/00507, filed on Sep. 19, 2000.

(51) Int. Cl.
*A61B 17/60*    (2006.01)

(52) U.S. Cl. ........................................ 606/80

(58) Field of Classification Search ................. 606/80, 606/79, 170, 180; 408/226, 231, 239 R
See application file for complete search history.

(56) References Cited

U.S. PATENT DOCUMENTS

| | | | |
|---|---|---|---|
| 4,813,808 A * | 3/1989 | Gehrke | 24/625 |
| 5,720,749 A | 2/1998 | Rupp | 606/69 |
| 5,941,891 A * | 8/1999 | Walen | 606/167 |
| 6,689,138 B1 * | 2/2004 | Lechot et al. | 606/80 |
| 6,783,533 B1 * | 8/2004 | Green et al. | 606/80 |

FOREIGN PATENT DOCUMENTS

| | | |
|---|---|---|
| DE | 198 13 699 | 12/1999 |
| WO | 88 03786 A | 6/1988 |

* cited by examiner

*Primary Examiner*—Eduardo C. Robert
*Assistant Examiner*—Jessica R. Baxter
(74) *Attorney, Agent, or Firm*—Jones Day

(57) ABSTRACT

The invention is directed to a device for the coupling of surgical instruments and/or implants such as a drive shaft and a reamer head. The device comprises a longitudinal male connector, and a hollow coupling shank having a first bore extending therethrough for receiving the male connector. The lateral portion of the male connector includes a plurality of flat surfaces, and the first bore shank includes a plurality of wall surfaces corresponding to the flat surfaces, so that the male connector can be inserted into the first bore to form a connection which is resistant to twisting about the longitudinal axis. The male connector defines a second bore extending coaxially therethrough and includes at least one radial slot, and defining a radially elastic, compressible holding element extending from the distal end. The male connector includes at least one radially protruding latch finger; and the first bore includes at least one latch finger recess to engage the latch finger so that the male connector can be axially fixed with respect to the shank. The latch finger and recess comprise disengagement means which permit disengagement by applying a disengagement tensile force on the male connector in the proximal direction.

20 Claims, 4 Drawing Sheets

COUPLING DEVICE FOR INSTRUMENT COMPONENTS

CROSS-REFERENCE TO RELATED APPLICATIONS

This application is a continuation of the U.S. national stage designation of copending International Patent Application PCT/CH00/00507, filed Sep. 19, 2000, the entire content of which is expressly incorporated herein by reference thereto.

FIELD OF THE INVENTION

The present invention relates generally to an apparatus for the coupling of instruments, in particular surgical instruments and/or implants such as a drive shaft and a reamer head.

BACKGROUND OF THE INVENTION

A coupling for connecting a reamer to a driving motor is described in U.S. Pat. No. 5,720,749. That reamer is used in particular to enlarge the medullary canals of bone and comprises essentially a cutting head detachably connectable to a flexible shaft linked to a source of rotational drive power. The elements of the coupling comprise, on the side of the cutting tool, a hollow tubular coupling shank and, on the side of the flexible shaft, a male connector insertable into the bore of said coupling shank. Both the hollow coupling shank and the male connector have essentially the form of a hollow cylindrical body, the outer lateral area of the male connector and the inner lateral area of the hollow coupling shank each having two parallel surfaces which correspond to each other and extend over a part of their lengths. On the male connector, these surfaces terminate short of the front end facing the coupling, so as to define two latch fingers on this end of the male connector. In addition, the wall of the male connector is provided with axial slots so as to define flexible arms. As the male connector is inserted into the hollow coupling shank, the two arms equipped with latch fingers are radially compressed until the male connector is completely inserted and the latch fingers engage with corresponding peripheral slots formed in the wall of the hollow coupling shank. Thus the male connector is rotationally and axially held in a fixed position within the hollow coupling shank. In order to remove the cutting head, the flexible arms of the male connector are compressed from outside of the hollow coupling shank by a compressive force applied through the peripheral slots thereof, so that the latch fingers disengage from these slots and the male connector can be pulled out of the hollow coupling shank. A disadvantage of this known apparatus consists in the necessity to have a special device for compressing the flexible arms from outside through the peripheral slots in order to be able to remove the cutting head. In addition, the connection between shaft and male connector is realized as a press-fitted engagement, which implies the disadvantage that a guide wire or Kirschner wire which may be inserted in the bore of the male connector can only be rotated with considerable friction loss.

A need exists for a coupling device to remedy these drawbacks and provide a coupling which allows the interconnectable parts to be joined together and removed without the aid of auxiliary instruments or devices. In addition, a need exists for a coupling that is made in such a way that when the parts are joined together, they will be firmly held against axial or rotational displacement in both directions.

SUMMARY OF THE INVENTION

The present invention is directed to a device for the coupling of surgical instruments and/or implants such as a drive shaft and a reamer head. The device comprises a longitudinal male connector having a proximal end, a distal end, a longitudinal axis, and a lateral portion, and a hollow coupling shank having a proximal end, a distal end, and a first bore extending therethrough for receiving the male connector coaxially to the longitudinal axis. The lateral portion of the male connector includes a plurality of flat surfaces extending parallel to the longitudinal axis. Each flat portion begins at a predetermined proximal distance from the distal end and extends therefrom in the proximal direction over a predetermined length, and the first bore shank includes a plurality of wall surfaces corresponding to the flat surfaces, so that the male connector can be inserted into the first bore to form a connection which is resistant to twisting about the longitudinal axis.

The male connector defines a second bore extending coaxially therethrough and includes at least one radial slot extending from the distal end in coaxial arrangement to the longitudinal axis to a predetermined depth, and defining a radially elastic, compressible holding element extending from the distal end. The male connector includes at least one radially protruding latch finger; and the first bore includes at least one latch finger recess to engage the latch finger so that the male connector can be axially fixed with respect to the shank. The latch finger and recess comprise disengagement means which permit disengagement by applying a disengagement tensile force on the male connector in the proximal direction, and the holding element may be radially compressed so that the latch finger will disengage from the recess and the male connector can be removed from the first bore.

In another embodiment, the device comprises a male connector and a hollow coupling shank including a bore for receiving said male connector, the lateral area of said male connector being equipped with n flats beginning at a distance A from the front end thereof and extending parallel to the longitudinal axis over a length L, the bore of the hollow coupling shank comprising n wall surfaces corresponding to said flats, so that the male connector can be received in the bore in a no-play engagement that prevents twisting about the longitudinal axis. The male connector comprises at least one radial slot extending from the front end to a depth T so as to define radially flexible arms extending from the front end to a depth T. In addition, the male connector comprises on its lateral area at least one latch finger situated near the front end thereof and protruding radially over the male connector or over at least one of said flats. The arms are radially compressible to such an extent that with compressed arms the male connector is insertable from the rear end of the hollow coupling shank into the part of the bore equipped with n wall surfaces and is capable of engaging with a recess formed in a portion of the bore corresponding to the latch finger, so that an axial blocking of the male connector in the hollow coupling shank can be achieved.

Said latch finger and said recess comprise means which permit that on applying on the male connector a tensile force of at least the amount X directed towards the rear end of the hollow coupling shank, the arms may be radially compressed to such an extent that the latch finger will disengage from the recess and the male connector can be removed from the hollow coupling shank. Preferably, the tensile force necessary for compressing the arms is between 1 and 50 N.

These means may consist, according to one embodiment, in an axially convex configuration of the latch fingers, or, according to further embodiments, in a configuration of the latch finger(s) in the form of a wedge with an angle a leading to at least one of the flats on the male connector.

The angle α may be, for all of the above-mentioned embodiments, between 15° and 85°, preferably between 25° and 35°.

In one embodiment, the male connector may be connected to a drive shaft rotatable about its longitudinal axis, whereas the hollow coupling shank may be connected for example to a reamer.

In another embodiment, the lateral area of the male connector has the shape of a circular cylindrical body and the latch fingers are formed by the creation of n flats on said lateral area, said flats being partly recessed in the radial direction relative to said lateral area. The recess has the form of a relieved portion and is situated adjacent to the part of the bore provided with said flats. The relieved portion is provided at the rear end with a first inner cone leading to the wall surfaces of the bore, half the cone angle of said first inner cone corresponding preferably to the angle α.

In a further embodiment, the end face of the relieved portion facing the front end is oriented orthogonally to the longitudinal axis and has the form of a flat end face. When the male connector is in an inserted position, the front end of the male connector abuts the end face of the relieved portion oriented orthogonally to the longitudinal axis.

In yet another embodiment, the at least one latch finger at the front end has the shape of a wedge extending parallel to the longitudinal axis and forming towards the front end an angle β relative to the longitudinal axis. The angle β may be, for all of the above-mentioned embodiments, between 15° and 85° preferably between 25° and 35°.

In a further embodiment, the relieved portion is provided at the front end with a second inner cone leading to the bore of the hollow coupling shank, half the cone angle of said inner cone corresponding preferably to the angle β. When the male connector is in an inserted position, the wedge-shaped latch fingers on the front end of the male connector abut said second inner cone of the relieved portion.

The axial lengths of said latch fingers and said relieved portion preferably correspond in such a way that when the latch fingers are in engagement with the relieved portion the male connector is axially blocked in both directions within the hollow coupling shank.

In yet another embodiment, the male connector has a bore extending concentrically to the longitudinal axis, which makes it possible to pass a guide wire or Kirschner wire through both the male connector and the hollow coupling shank. In another embodiment, the male connector in its longitudinal segment has a polygonal cross section. In another embodiment the wall surfaces form axially arranged, wedge-shaped enlargements leading to the rear end of the hollow coupling shank.

One skilled in the art will appreciate that the device advantageously permits connection and disconnection of two components of a surgical instrument in a simple manner and without the help of auxiliary devices. In addition, it is possible while the components are in a connected condition to pass a guide wire or Kirschner wire through the male connector and the hollow coupling shank without the occurrence of friction losses when the apparatus is rotated relative to the guide wire or Kirschner wire. Also, when the components are coupled together, the apparatus prevents twisting and axial displacement of the male connector relative to the hollow coupling shank.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
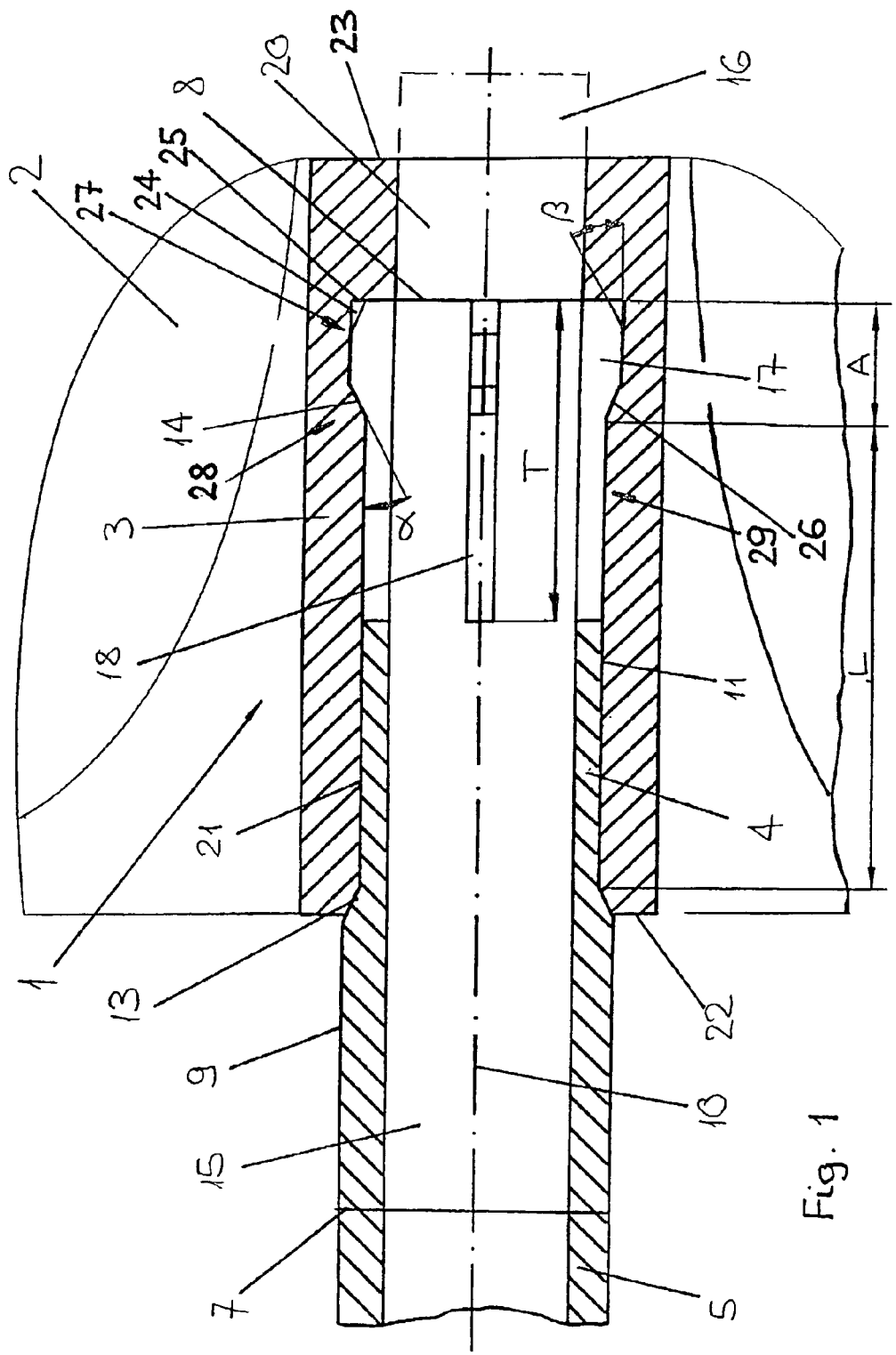
FIG. 1 is a longitudinal sectional view of the preferred embodiment of the apparatus according to the present invention.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

Figure 2:
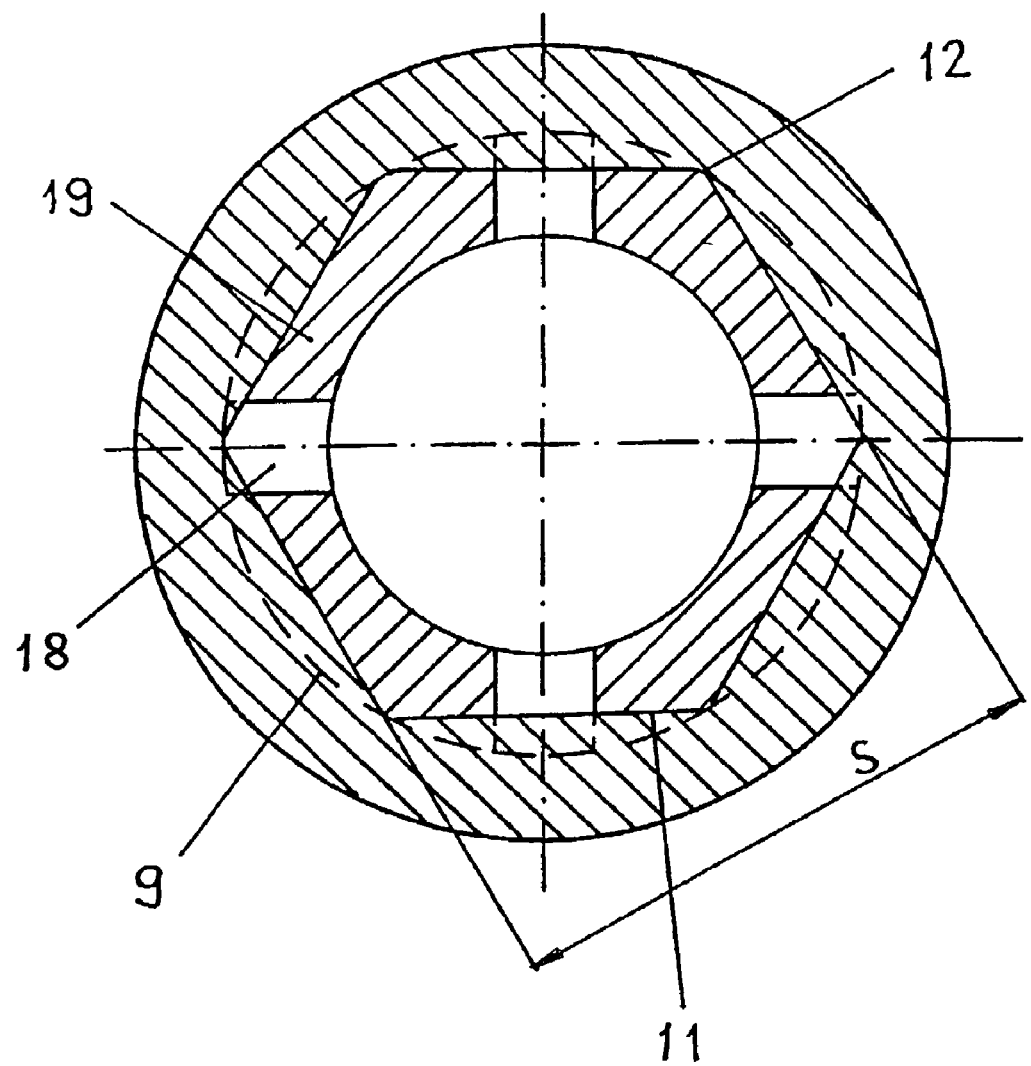
FIG. 2 is a cross section of the embodiment of the apparatus according to the invention shown in FIG. 1.

FIGS. 1 and 2 show sectional views of one preferred embodiment of the coupling 1 according to the invention. By means of the coupling 1, a hollow coupling shank 3 equipped for example with the cutting head 2 of a reamer is detachably connected to a male connector 4 of a flexible drive shaft 5, the hollow coupling shank 3 and male connector 4 are preferably rotatively and axially blocked or fixed relative to each other when the coupling is in a connected condition. Male connector 4 has the shape of a hollow cylindrical body and has a longitudinal axis 10, a proximal or rear end 7 facing the shaft and a distal or front end 8 opposite to the drive shaft 5. The axial bore 15 provided in the male connector 4 serves for receiving a guide wire or Kirschner wire 16. The outer lateral area 9 of male connector 4 has the form of a circular cylinder with a diameter D and is provided with six flats 11 extending symmetrically to the longitudinal axis 10 in a hexagonal arrangement. The width S across parallel flats 11 of the hexagonal arrangement is smaller than the diameter D of the male connector 4 and is dimensioned in such a way that rounded edges 12 are formed on the outer lateral area 9 between two adjacent flats 11. In addition, male connector 4 is provided with four slots 18 arranged symmetrically about the circumference of the male connector 4, beginning from the front end 8 and extending parallel to longitudinal axis 10 to a depth T, so as to form four radially flexible arms 19. In the direction of the longitudinal axis, the flats 11 have a length L which, beginning at a distance A in the proximal direction from the front end 8, extends towards the rear end 7, so that on the portion of the outer lateral area 9 extending from the front end 8 to the distance A latch fingers 17 are formed. Transition segments 13 and 14 are formed obliquely in relation to longitudinal axis 10 between flats 11 and outer lateral area 9 and are wedge-shaped. The front transition segment 14 leads to latch fingers 17, and longitudinal axis 10 forming an angle α of 30°. The latch fingers 17 situated on front end 8 parallel to longitudinal axis 10 are wedge-shaped and form an angle β of 30° with respect to longitudinal axis 10.

Hollow coupling shank 3 has a proximal or rear end 22 toward the shaft, a distal or front end 23 opposite therefrom, and a bore 20 extending therethrough. Within bore 20 and in alignment with longitudinal axis 10, shank 3 includes six wall surfaces 21 extending maximally over the length L and corresponding to the flats 11 of the male connector 4. Towards the front end 23 and adjoining wall surfaces 21, bore 20 of the hollow coupling shank 3 is equipped with a relieved portion 24. End face 25 of relieved portion 24 faces front end 23 and is oriented orthogonally to longitudinal axis 10. Toward rear end 22, relieved portion 24 defines a first inner cone 26 that leads to the wall surfaces 21. Half the cone angle of inner cone 26 corresponds to angle α of the transition segment 14 of latch fingers 17. The wall surfaces 21 form wedge-shaped enlargements extending parallel to the longitudinal axis 10 and leading to the rear end 22 of the hollow coupling shank 3. The angle of the wedges preferably correspond to angle β and are preferably equal to about 30°.

With the aforementioned configuration of hollow coupling shank 3 and male connector 4, the male connector 4 can be inserted into bore 20 from the rear end 22 of the hollow coupling shank 3, and latch fingers 17 which protrude radially over wall surfaces 21 are insertable into the hollow coupling shank 3 by means of radial compression of flexible arms 19. Once male connector 4 is inserted sufficiently into bore 20 for the latch fingers 17 to reach the area of relieved portion 24, the arms 19 will recover or expand to their uncompressed condition and the latch fingers 17 will engage the relieved portion 24. When the male connector 4 is completely inserted into the hollow coupling shank 3, the contact of front end 8 with end face 25 of the relieved portion 24 assures an axial stop against the front end 23 of the hollow coupling shank 3, and the inner cone 26 and the transition segments 14 cause an axial blocking of the male connector 4 against the rear end 22 of the hollow coupling shank 3. If the width of latch fingers 17 as defined by the distance A corresponds to the width of the relieved portion 24, the male connector 4, once completely engaged, is blocked against axial displacements in both directions. In addition, the combined effect of the wedge-shaped form of transition segment 14 on the male connector 4 and of the inner cone 26 on the relieved portion 24 allows the flexible arms 19 to be radially compressed when a tensile force in the direction of the rear end 22 of the hollow coupling shank 3 is exerted on the male connector 4, which makes it possible for latch fingers 17 to disengage from the relieved portion 24 so that male connector 4 may be drawn out of the hollow coupling shank 3. The angles α of first inner cone 26 and of transition segment 14 are preferably chosen in such a way that the axial force necessary for compressing the flexible arms 19 is greater than that occurring during normal use of the instrument. In addition, the flexible arms 19 cannot be inwardly displaced when a guide wire or Kirschner wire 16 has been introduced into the bore 15 of the male connector 4, so that during normal use of the instrument the male connector 4 is additionally blocked against the rear end 22 of the hollow coupling shank 3.

Figure 3:
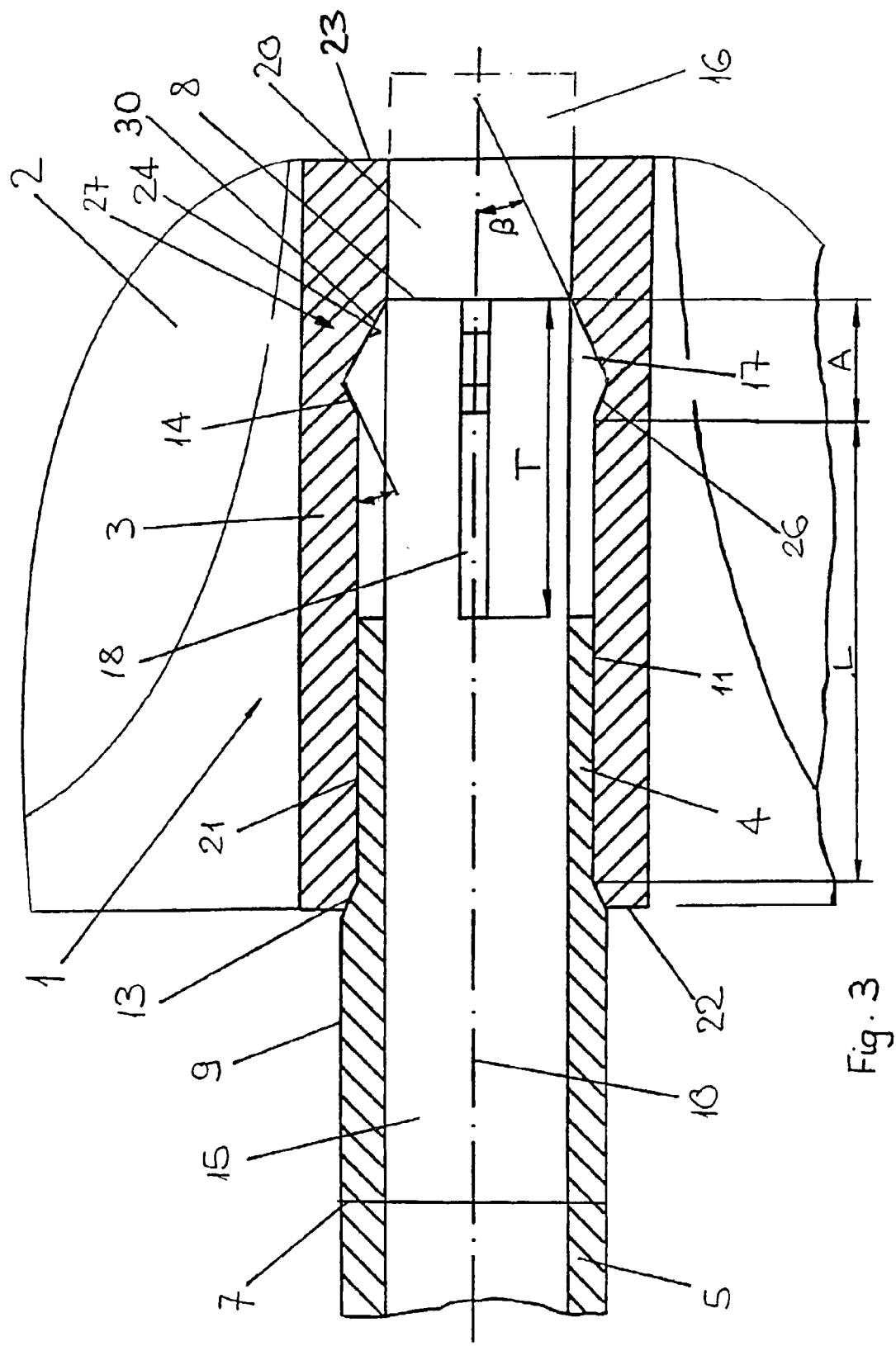
FIG. 3 is a longitudinal sectional view of another embodiment of the apparatus according to the invention.

FIG. 3 shows another embodiment of the apparatus according to the invention. The embodiment of FIG. 3 differs from the embodiment of FIG. 1 in so far as relieved portion 24 at front end 23 of hollow coupling shank 3 has a second inner cone 26 leading to bore 20, and half the cone angle of second inner cone 26 corresponds to angle β.

Figure 4:
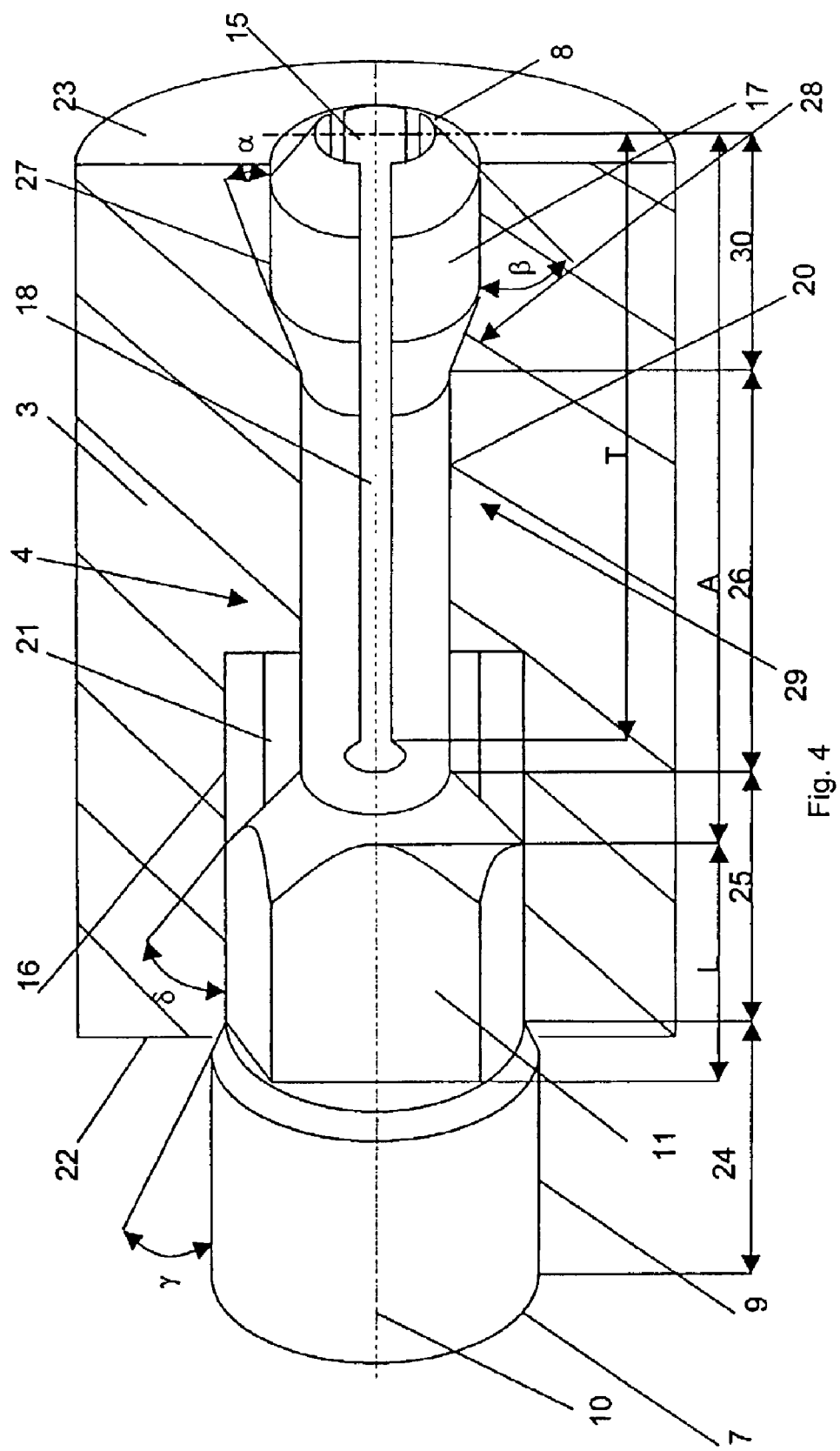
FIG. 4 is a perspective view of a male connector including a sectional view of a hollow coupling shank of a further embodiment of the apparatus according to the invention.

FIG. 4 shows another embodiment of the apparatus according to the invention which differs from the embodiment shown in FIGS. 1 and 2 in so far as the male connector 4 comprises four axially adjacent, coaxial segments 24, 25, 26, and 30 between the rear end 7 and the front end 8. The first segment 24, adjacent rear end 7 is in the form of a circular cylinder and is connectable on rear end 7 to a drive shaft (not shown). Directed towards front end 8, second segment 25 adjoins first segment 24. The second segment 25 has a prismatic form with a hexagonal cross section, and the width across corners of the hexagon are smaller than the outside diameter of first segment 24. The transition segment leading from first segment 24 to second segment 25 is conically shaped and preferably half the cone angle γ is about 45°. A third segment 26 follows and adjoins second segment 25 further toward front end 8, and has the shape of a circular cylinder with an outer diameter that is smaller than the width across the flats of the hexagonally shaped second segment 25. The transition segment between the second segment 25 and the third segment 26 is also conically shaped preferably with half a cone angle δ of about 45°. Fourth segment 30 adjoins the third segment 26 and extends to the front end 8, and has a greater outside diameter than the third segment 26. A transition segment between third segment 26 and fourth segment 30 is conical and preferably has half a cone angle α of about 30°. The opposite end of fourth segment 30 conically terminates at the front end 7 preferably with half a cone angle β of about 30°. Male connector 4 comprises a coaxial bore 15 extending from front end 8 to a depth T as well as three slots 18 equally extending from front end 8 to a depth T and interrupting the continuity of the wall of the male connector 4 in a direction parallel to the longitudinal axis 10 between bore 15 and outer lateral area 9. By means of slots 18, a radial compressibility of male connector 4 along the depth T is achieved and in this axial segment the male connector 4 assumes the function of a radially elastic holding element 29. Due to the greater outside diameter of the fourth segment 30 relative to the third segment 26 and due to the radially offset and slotted wall of the male connector 4, three latch fingers 17, radially protruding from the third segment 26, are formed.

The hollow coupling shank 3 is shaped complementary to the male connector 4 and is connectable on front end 23 to a surgical instrument (not shown). Bore 20 has a hexagon socket 16, located towards rear end 22 of the hollow coupling shank 3, which forms a connection that is resistant to twisting about the longitudinal axis 10 when the hollow coupling shank 3 is joined together with second segment 25 of male connector 4. Hexagon socket 16 is provided with a cone segment complementary to the conical transition segment located between first segment 24 and second segment 25 and leads to the end face on rear end 22 of the hollow coupling shank 3. Toward front end 23 of the hollow coupling shank 3, the bore 20 comprises a circularly cylindrical recess 27 including a frustoconical segment separating recess 27 from bore 20 and conically leading to bore 20, the shape of said segment being complementary to the conical transition segment between third segment 26 and fourth segment 30. As front end 8 of the male connector 4 is inserted into the bore 20 of the hollow coupling shank 3, radially elastic holding element 29 of male connector 4 is radially compressed so that latch fingers 17 may glide axially through the circularly cylindrical middle portion of bore 20 towards front end 23 of hollow coupling shank 3 until the latch fingers reach recess 27 where the elastic holding element 29 may regain its initial, uncompressed condition, and the latch fingers 17 engage recess 27. Thus, male connector 4 is lodged in hollow coupling shank 3 by means of a connection which is resistant to twisting and fixed or blocked against axial displacement relative to longitudinal axis 10. If a sufficiently great tensile force acting in the direction of rear end 23 of hollow coupling shank 3 is applied on male connector 4, latch fingers 17 are radially compressed due to the combined effect of the complementary conical transition segments between, on the one hand, the third and fourth segments 26, 30 of the male connector 4 and, on the other hand, the bore 20 and the recess 27, so that the male connector 4 may be pulled axially towards rear end 23 of hollow coupling shank 3 and removed therefrom.

What is claimed is:

1. A device for coupling instruments comprising:
   a longitudinal male connector having a proximal end, a distal end, a longitudinal axis, and a lateral portion;
   a hollow coupling shank having a proximal end, a distal end, and a first bore extending therethrough for receiving the male connector coaxially to the longitudinal axis,
   wherein the lateral portion of the male connector includes a plurality of flat surfaces extending parallel to the longitudinal axis, each flat portion beginning at a predetermined proximal distance from the distal end and extending therefrom in the proximal direction over a predetermined length, and the first bore shank includes a plurality of wall surfaces corresponding to the flat surfaces, so that the male connector can be inserted into the first bore to form a connection which is resistant to twisting about the longitudinal axis,
   wherein the male connector defines a second bore extending coaxially therethrough and at least one radial slot extending from the distal end in coaxial arrangement to the longitudinal axis to a predetermined depth, and defining a radially elastic, compressible holding element extending from the distal end,
   wherein the male connector includes at least one radially protruding latch finger; and the first bore includes at least one latch finger recess to engage the latch finger so that the male connector can be axially fixed with respect to the shank, and the latch finger and recess comprise disengagement means which permit disengagement by applying a disengagement tensile force on the male connector in the proximal direction, and the holding element may be radially compressed so that the latch finger will disengage from the recess and the male connector can be removed from the first bore.

2. The device of claim 1, wherein the proximal end of the male connector is connected to a drive shaft.

3. The device of claim 2, wherein the hollow coupling shank is connected to a reamer.

4. The device of claim 3, wherein said disengagement means comprise an axially convex shape of the at least one latch finger.

5. The device of claim 3, wherein at least one latch finger comprises a wedge-shaped portion including a proximal surface extending at a first an angle with respect to the longitudinal axis.

6. The device of claim 5, wherein the at least one latch finger comprises a wedge-shaped portion including a distal surface located adjacent the distal end of the male connector extending at a second angle with respect to the longitudinal axis.

7. The device of claim 6, wherein the male connector includes a plurality of latch fingers.

8. The device of claim 7, wherein the second angle is between about 15° and about 85°.

9. The device of claim 7, wherein the second angle is between about 25° and 35°.

10. The device of claim 6, wherein the first angle is between about 15° and about 85°.

11. The device of claim 6, wherein the first angle is between about 25° and about 35°.

12. The device of claim 1, wherein the disengagement tensile force is between 1 and 50 N.

13. The device of claim 1, wherein the recess has the form of a relieved portion.

14. The device of claim 13, wherein the relieved portion has a first inner cone leading to the wall surface.

15. The device of claim 14, wherein half the cone angle of the first inner cone corresponds to the first angle.

16. The device of claim 15, wherein the relieved portion has an end face which faces the distal end of the shank and is oriented orthogonally to the longitudinal axis.

17. The device of claim 15, wherein the relieved portion has a second inner cone adjacent the distal end of the shank and leading to the bore.

18. The device of claim 17, wherein half the cone angle of said second inner cone corresponds to the second angle.

19. The device of claim 18, wherein the male connector has a bore extending concentrically to the longitudinal axis through its entire length, so that a guide wire may be passed concentrically to the longitudinal axis through both the male connector and the hollow coupling shank.

20. The device of claim 1, wherein the male connector has a longitudinal segment with a hexagonal cross section.

* * * * *